US012805812B2

(12) United States Patent
Yokobori

(10) Patent No.: US 12,805,812 B2
(45) Date of Patent: Nov. 24, 2026

(54) RELAY APPARATUS OF MEDICAL SYSTEM, CONTROL METHOD FOR RELAY APPARATUS OF MEDICAL SYSTEM, AND MEDICAL SYSTEM

(71) Applicant: OLYMPUS MEDICAL SYSTEMS CORP., Tokyo (JP)

(72) Inventor: Shoichi Yokobori, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 81 days.

(21) Appl. No.: 19/082,784

(22) Filed: Mar. 18, 2025

(65) Prior Publication Data

US 2025/0213203 A1 Jul. 3, 2025

Related U.S. Application Data

(63) Continuation of application No. PCT/JP2022/035430, filed on Sep. 22, 2022.

(51) Int. Cl.
*A61B 5/00* (2006.01)
*A61B 5/024* (2006.01)

(52) U.S. Cl.
CPC .............. *A61B 5/746* (2013.01); *A61B 5/024* (2013.01)

(58) Field of Classification Search
CPC ....... A61B 5/746; A61B 5/024; A61B 5/0002; A61B 1/00
See application file for complete search history.

(56) References Cited

U.S. PATENT DOCUMENTS

2008/0242983 A1 10/2008 Hibi
2011/0205031 A1* 8/2011 Wakabayashi .......... H04L 12/12 340/10.41
2017/0318165 A1 11/2017 Ogata et al.
2021/0298853 A1 9/2021 Miyamoto et al.

FOREIGN PATENT DOCUMENTS

JP 2003334164 A 11/2003
JP 2005296198 A 10/2005
JP 2008245789 A 10/2008
JP 2012010940 A 1/2012
JP 2016174221 A 9/2016
WO 2020021870 A1 1/2020

OTHER PUBLICATIONS

International Search Report dated Dec. 13, 2022 received in PCT/JP2022/035430.

* cited by examiner

*Primary Examiner* — Thomas S Mccormack
(74) *Attorney, Agent, or Firm* — Scully, Scott, Murphy & Presser, P.C.

(57) ABSTRACT

A relay apparatus of a medical system including: a reception unit that receives a heartbeat signal from a controller of the medical system, and after receiving a first signal that continuously changes a set value of a medical device of the medical system, receives the heartbeat signal at a shorter interval than an interval before receiving the first signal; a conversion unit that converts the first signal into a second signal; a transmission unit that transmits the second signal to the medical device; a detection unit that detects a communication disconnection between the relay apparatus and the controller, based on the heartbeat signal received at the shorter interval; and a control unit that controls the transmission unit to transmit a third signal, which is a fail-safe signal, to the medical device, based on a detection signal received from the detection unit.

12 Claims, 6 Drawing Sheets

RELAY APPARATUS OF MEDICAL SYSTEM, CONTROL METHOD FOR RELAY APPARATUS OF MEDICAL SYSTEM, AND MEDICAL SYSTEM

CROSS-REFERENCE TO RELATED APPLICATION

This application is a continuation application of PCT/JP2022/035430 filed on Sep. 22, 2022, the entire contents of which are incorporated herein by this reference.

BACKGROUND OF THE INVENTION

1. Field of the Invention

The present disclosure relates to a relay apparatus of a medical system, which is configured to convert a first signal outputted from a controller of the medical system into a second signal and output the second signal to a medical device of the medical system, a control method for the relay apparatus of the medical system, and the medical system including the controller, the relay apparatus, and the medical device.

2. Description of the Related Art

In endoscopic surgery, etc., in addition to an endoscope apparatus, a large number of medical devices, such as a pneumoperitoneum device, an electric scalpel, etc., are used. A medical system including a plurality of medical devices performs centralized control of the plurality of medical devices by a system controller.

Even medical devices included in one medical system usually use different communication protocols. For this reason, a relay apparatus configured to perform protocol conversion is disposed between a system controller and the medical devices.

Japanese Patent Application Laid-Open Publication No. 2008-245789 discloses a medical system including a system controller configured to perform protocol conversion to communicate with medical devices.

Japanese Patent Application Laid-Open Publication No. 2005-296198 discloses a medical system including a system controller configured to detect a status of communication between itself and a medical device. Based on a result of the detection, if communication has not been performed for a predetermined time period, the system controller stops driving of the medical device.

Japanese Patent Application Laid-Open Publication No. 2003-334164 discloses a medical system including a system controller, and when the system controller detects an abnormality based on an abnormality signal outputted from a medical device, the system controller notifies the occurrence of the abnormality.

A system controller of a medical system sometimes outputs a signal that continuously changes a set value of a medical device for the purpose of improving an operational efficiency. For example, in a case where a set value of an output of an electric scalpel is increased to a predetermined value, it is more efficient to increase the set value at a predetermined rate (for example, +1/0.2 seconds) with a single button operation than to repeat operation to increase the set value by "1" with a single button operation.

For example, a long press (hold down) operation of continuously pressing the button is performed to cause a signal that continuously changes the set value to be outputted. When the set value reaches the predetermined value, the button press is released to thereby cause a stop signal that stops an increase of the set value to be outputted.

SUMMARY OF THE INVENTION

A relay apparatus of a medical system according to an aspect of the present disclosure, includes: a reception unit configured to receive a heartbeat signal from a controller of the medical system, the reception unit being configured to, after receiving a first signal that continuously changes a set value of a medical device of the medical system, receive the heartbeat signal at a shorter interval than an interval before receiving the first signal; a conversion unit configured to convert the first signal into a second signal; a transmission unit configured to transmit the second signal to the medical device; a detection unit configured to detect a communication disconnection between the relay apparatus and the controller, based on the heartbeat signal received at the shorter interval; and a control unit configured to control the transmission unit to transmit a third signal, which is a fail-safe signal, to the medical device, based on a detection signal received from the detection unit.

A control method for a relay apparatus of a medical system according to an aspect of the present disclosure includes: receiving a heartbeat signal from a controller of the medical system, and upon reception of a first signal that continuously changes a set value of a medical device of the medical system, receiving the heartbeat signal at a shorter interval than an interval before the reception of the first signal; converting the first signal into a second signal; transmitting the second signal to the medical device; and upon detection of a communication disconnection based on the heartbeat signal received from the controller at the shorter interval, transmitting a third signal, which is a fail-safe signal, to the medical device.

A medical system according to an aspect of the present disclosure includes: a medical device; a controller configured to transmit a heartbeat signal, the controller being configured to, after transmitting a first signal that continuously changes a set value of the medical device, transmit the heartbeat signal at a shorter interval than an interval before transmitting the first signal; and a relay apparatus configured to: receive the first signal to convert the received first signal into a second signal; transmit the second signal to the medical device; and upon detection of a communication disconnection between the relay apparatus and the controller based on the heartbeat signal received at the shorter interval, transmit a third signal, which is a fail-safe signal, to the medical device.

DETAILED DESCRIPTION OF THE PREFERRED EMBODIMENT(S)

Hereinafter, an embodiment of the present disclosure will be described with reference to drawings.

FIRST EMBODIMENT

<Configuration of Medical System>

Figure 1:
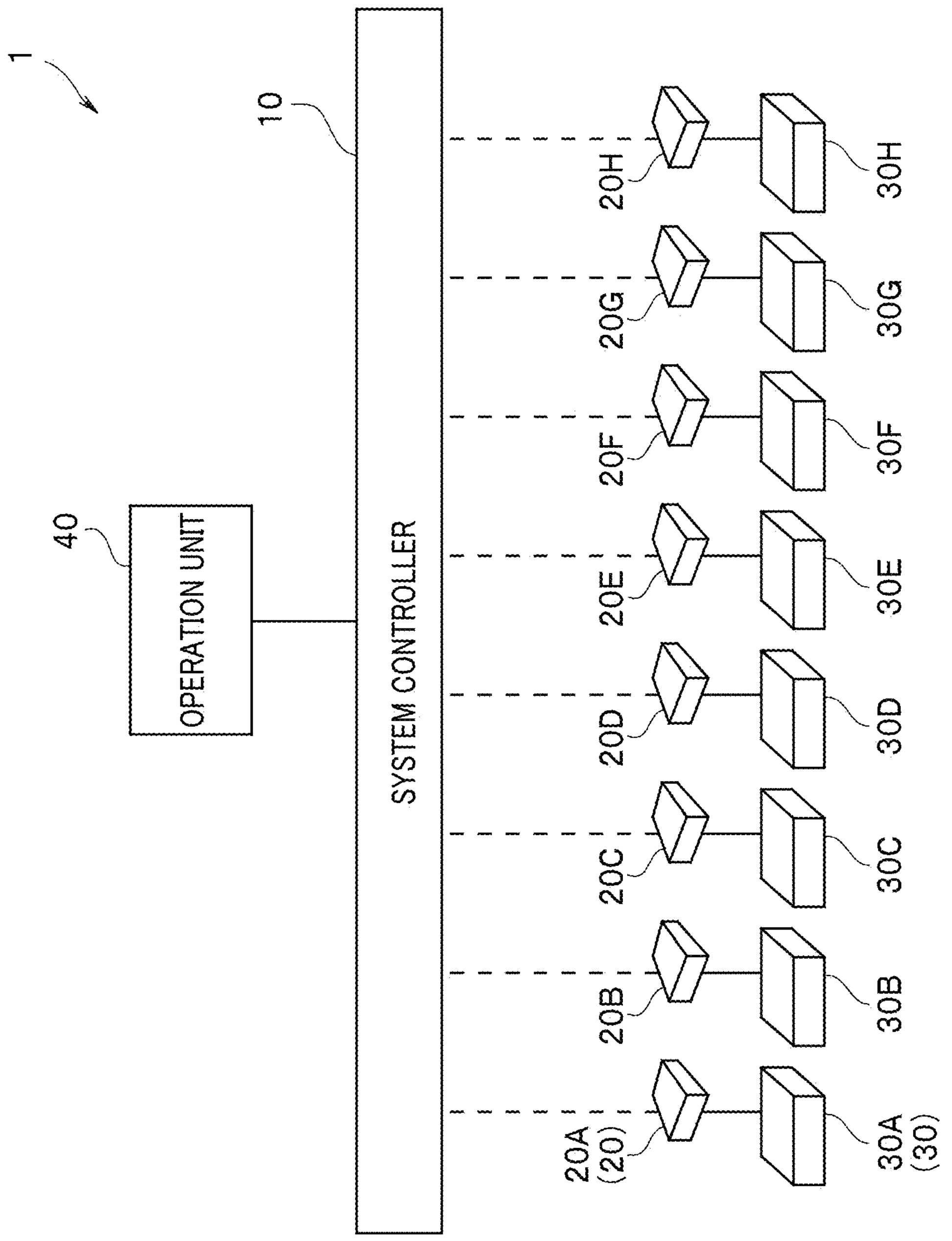
FIG. 1 is a configuration view of a medical system of an embodiment.

A medical system 1 of the present embodiment as shown in FIG. 1 includes a system controller 10 (hereinafter, referred to as "controller 10"), a plurality of relay apparatuses 20 (20A-20H), a plurality of medical devices 30 (30A-30H), and an operation unit 40. In the medical system 1, one relay apparatus 20 is provided for each of the medical devices 30.

The medical system 1 includes, as medical devices 30 which are peripheral devices, a video processor 30A, a light source apparatus 30B, a $CO_2$ feeding device 30C, an electric scalpel device 30D, an operation table unit 30E, a shadowless lamp unit 30F, a pneumoperitoneum device 30G, and an ultrasonic coagulation incision device 30H.

The video processor 30A connected to an endoscope (not shown) is configured to process an endoscopic video. The light source apparatus 30B is configured to generate illumination light for the endoscope. The $CO_2$ feeding device 30C is configured to feed $CO_2$ to an inside of a digestive organ, and the like. The electric scalpel device 30D is an electric coagulation incision device. The operation table unit 30E includes an operation bed and a control kit thereof. The shadowless lamp unit 30F includes a light that illuminates a surgical field in an operation without creating a shadow, and a control kit thereof. The pneumoperitoneum device 30G is a device for inflating an inside of an abdominal cavity with gas. The ultrasonic coagulation incision device 30H is a coagulation incision device using ultrasonic vibration.

Figure 2:
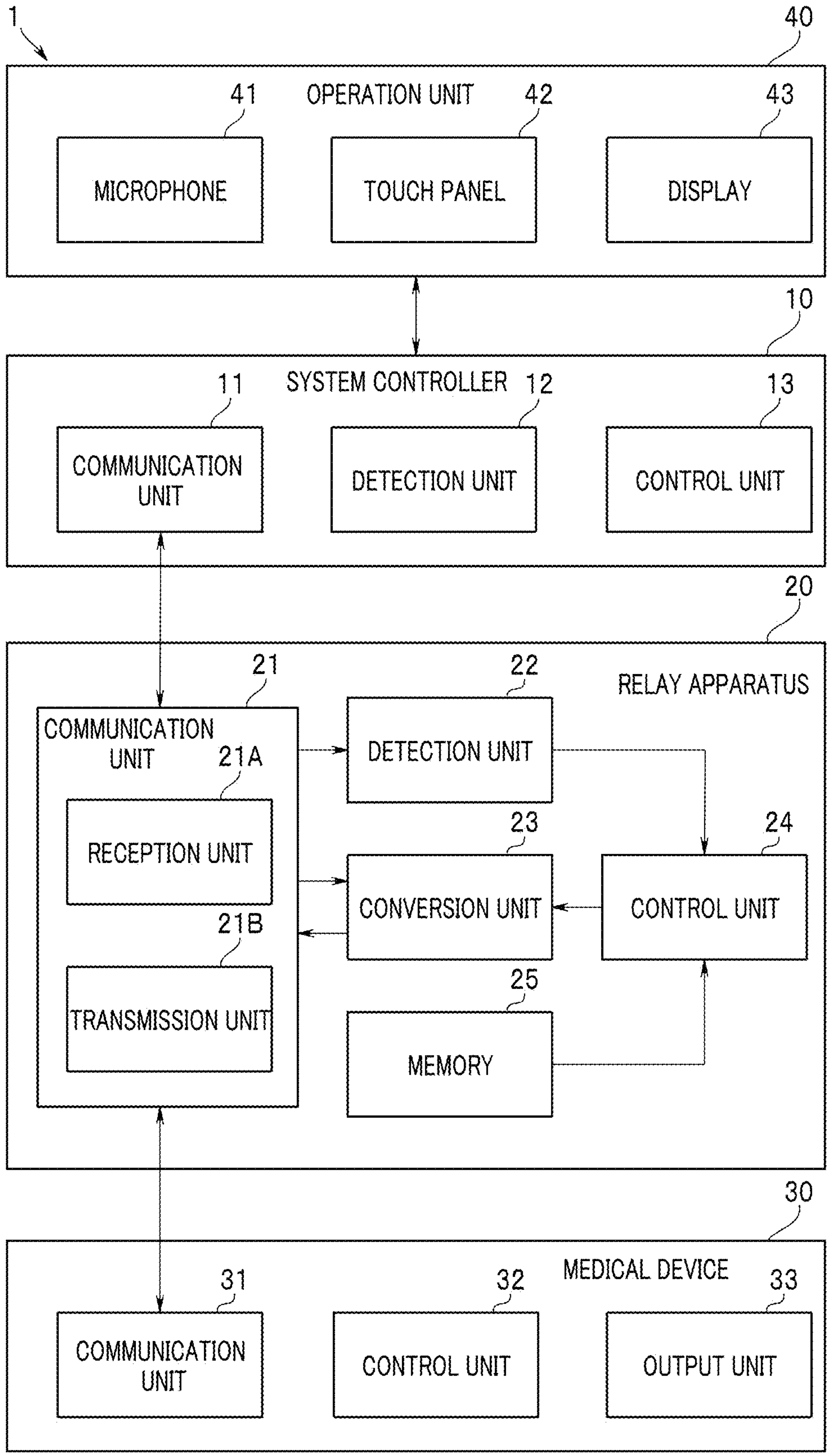
FIG. 2 is a configuration view of the medical system of the embodiment.

As shown in FIG. 2, the operation unit 40 is an operation means for an operator to input the settings of the medical devices 30 into the controller 10 through a microphone 41 and a touch panel 42. The operation unit 40 includes a display 43 that displays an endoscopic image, operation states of the plurality of medical devices 30, and the like. The display 43 may serve also as the touch panel 42. The operation unit 40 may include a plurality of touch panels 42 and a plurality of displays 43.

The controller 10 includes a communication unit 11, a detection unit 12, and a control unit 13. The control unit 13 generates a signal (command) for controlling each of the medical devices 30, based on the operation data from the operation unit 40, and the communication unit 11 wirelessly transmits the command to the relay apparatus 20. As described later, the detection unit 12 detects the communication state between the controller 10 and the medical devices 30.

The control signal includes data indicating that the signal is for which of the medical devices 30. The data for identifying the medical devices 30 include device IDs for the medical devices 30, for example. In the medical system configured such that a plurality of medical devices 30 are connected to one relay apparatus 20, the control signal may include information indicating, among the ports of the relay apparatus 20, a port to which each of the medical devices 30 is connected, and other information.

The relay apparatus 20 includes a communication unit 21 (a reception unit 21A and a transmission unit 21B), a detection unit 22, a conversion unit 23, a control unit 24, and a memory 25. The control unit 24 controls the operation of the entire relay apparatus 20.

The relay apparatus 20 (20A-20H) is a communication converter configured to perform protocol conversion in accordance with the medical device 30, on the control signal to the medical device 30 (30A-30H), which has been received from the controller 10 as a host. A known technique is used for the protocol conversion processing to be performed by the conversion unit 23. The conversion methods in accordance respectively with the plurality of medical devices 30A to 30H are stored in the memory 25.

Note that the detection unit 12 of the controller 10 uses the communication unit 11, to transmit a heartbeat signal periodically (every two seconds, for example) to the relay apparatus 20 and receive a response signal in response to the heartbeat signal from the relay apparatus 20, in order to confirm whether the communication connection between the controller 10 and the relay apparatus 20 is active. The detection unit 22 of the relay apparatus 20 uses the communication unit 21, to receive the heartbeat signal transmitted periodically from the controller 10 and transmit the response signal to the controller 10. The communication unit 21 of the relay apparatus 20 may transmit the heartbeat signal and the communication unit 11 of the controller 10 may transmit the response signal.

In the medical system 1 of the present embodiment, a wired connection is established between the operation unit 40 and the controller 10, and between the relay apparatus 20 and the medical device 30, while a wireless connection is established between the controller 10 and the relay apparatus 20. Note that the connection between the operation unit 40 and the controller 10, the connection between the controller 10 and the relay apparatus 20, and the connection between the relay apparatus 20 and the medical device 30 may be established by wire or wirelessly.

When the controller 10 and the relay apparatus 20 are connected wirelessly, the detection units 12 and 22 may confirm whether communication connection is active based on the strength of the wireless signal (RSSI), instead of the heartbeat signal. When the strength of the wireless signal is smaller than a predetermined value, the detection units can determine that the communication is disconnected.

The medical device 30 includes a communication unit 31, a control unit 32, and an output unit 33. The control unit 32 controls the output unit 33, based on the control signal received via the communication unit 31.

As described later, in the medical system 1, even if the communication between the controller 10 and the relay apparatus 20 is disconnected after the controller 10 transmits the signal (first signal) that continuously changes the set value of the medical apparatus 30, the relay apparatus 20 transmits a third signal that causes the medical device 30 to perform a fail-safe operation to the medical device 30. The fail-safe operation is an operation on the safe side assumed at the time of the design.

With such a fail-safe operation, in the medical system 1, the set value of the medical device 30 is prevented from being changed beyond the user's intended value.

<Operation Method for Medical System>

Figure 3:
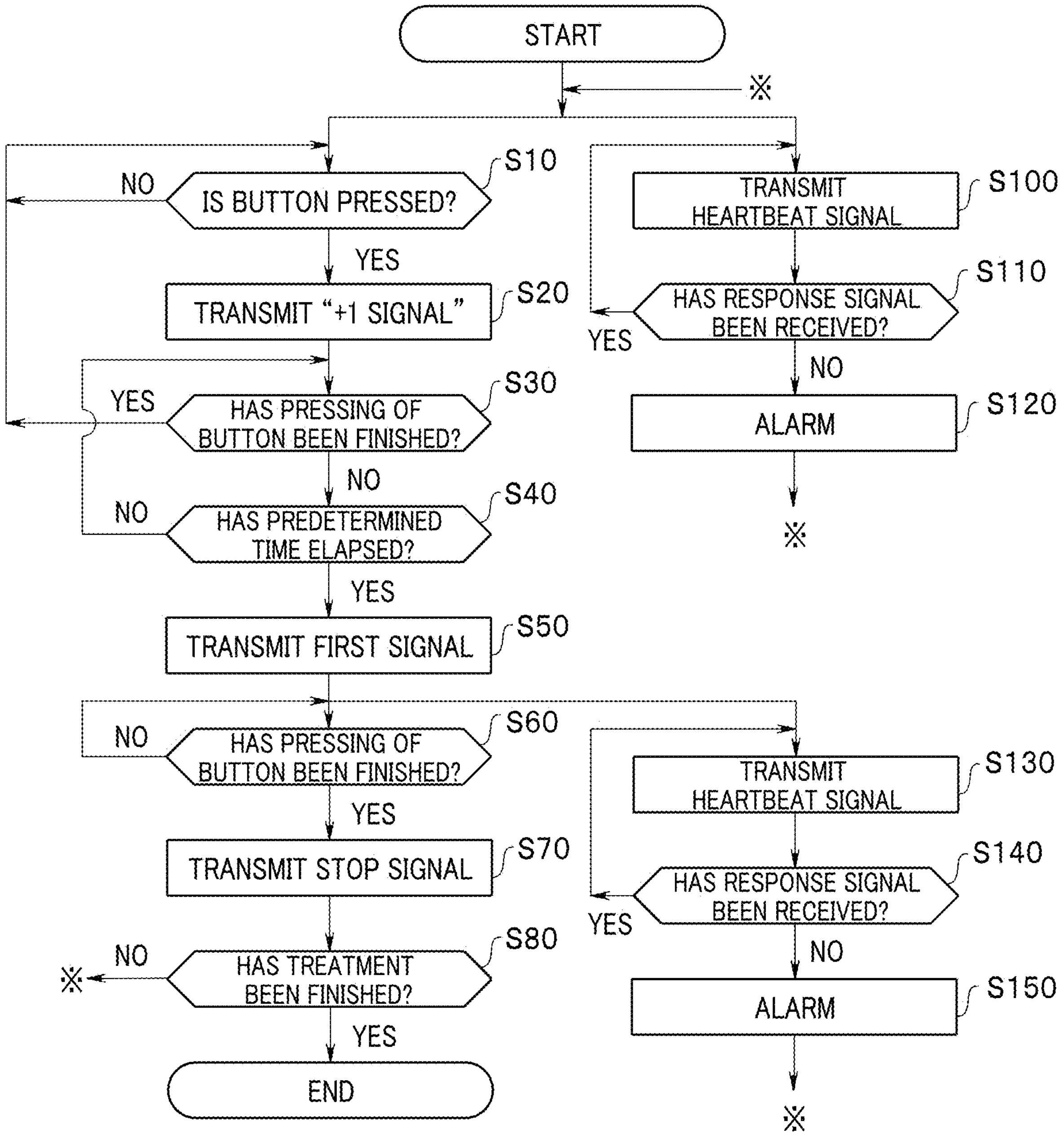
FIG. 3 is a flowchart of a normal operation of the medical system of the embodiment.

First, a normal operation of the controller 10 will be described with reference to the flowchart in FIG. 3.

When the medical system 1 is activated, a system check is performed. Then, an operation screen corresponding to the medical device 30 that is being connected is displayed on the touch panel 42, for example.

<Step S10>

Figure 4:
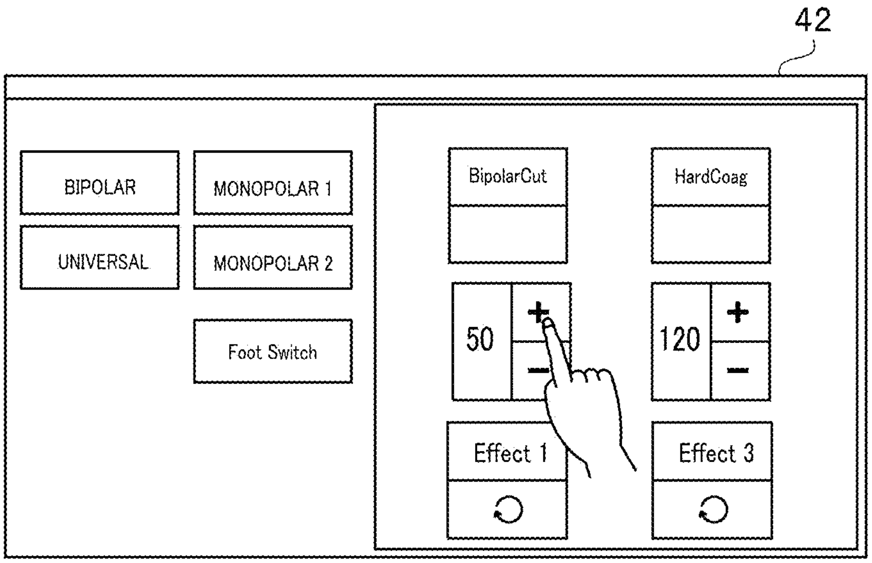
FIG. 4 is a view showing a touch panel operation of the medical system of the embodiment.
Figure 5:
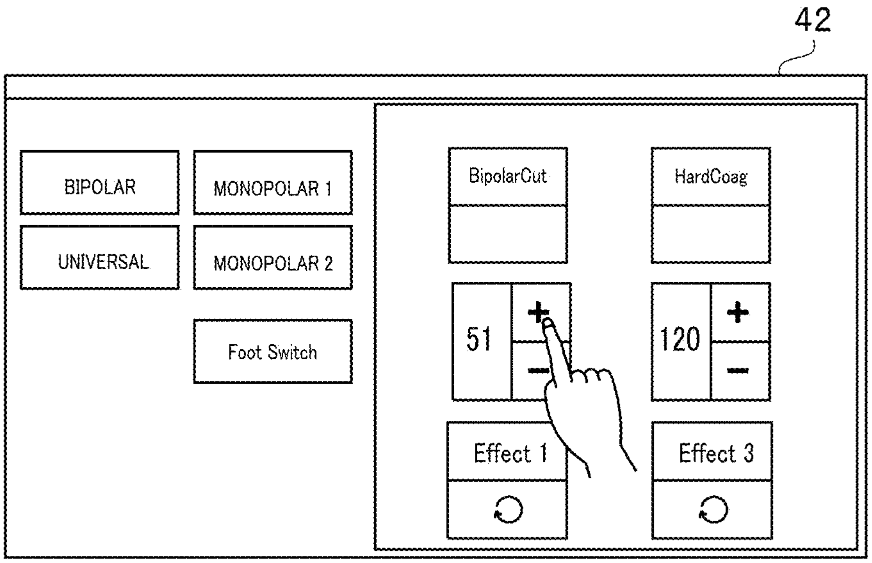
FIG. 5 is a view showing the touch panel operation of the medical system of the embodiment.

FIG. 4 and FIG. 5 each show an example of an operation screen for the electric scalpel device 30D displayed on the touch panel 42. When a user increases the output value of the electric scalpel device 30D from "50", the user presses "+ button" with their finger. Strictly speaking, the "pressing operation" on the touch panel 42 is a "touch operation".

<Step S20>

The controller 10 transmits to the relay apparatus 20 "+1 signal" to increase the set value of the electric scalpel device 30D by 1.

<Step S30>

When the user finishes pressing the "+ button" (releases their finger from the "+ button" on the touch panel 42) (S30, YES), the processing returns to the step S10, and the controller 10 waits until the "+ button" on the touch panel 42 is pressed again.

Each time the user touches the "+ button" once on the touch panel 42 of the operation unit 40, the controller 10 transmits the "+1 signal" once.

<Step S40, S50>

On the other hand, when the button is pressed long, that is, when the user has not finished pressing the "+ button" (the user has not released their finger from the button) even after a predetermined time period T1 (for example, one second) elapsed (S40, YES), the controller 10 transmits the signal (first signal) that continuously increases the set value of the electric scalpel device 30D to the relay apparatus 20 (S50). The first signal is a control signal that continuously increases the set value at a predetermined rate (for example, +1/0.2 seconds).

<Step S60, S70>

When the user finishes pressing the "+ button" (releases their finger from the button) (S60, YES), the controller 10 transmits to the relay apparatus 20 a stop signal that stops the continuous increase of the set value of the electric scalpel device 30D (S70).

<Step S80>

Until the treatment is finished (S80: YES), the processing will be repeated from the step S10. For example, the user continuously increases the set value up to 100 (+100) by the long press operation of the button, and further repeats the operation of increasing the set value by 1 (+1) five times, to thereby be able to set the set value to 105 (+105) rapidly, easily, and accurately.

Note that the controller 10 repeats the transmission of the heartbeat signal (S100, S130) and the reception of the response signal from the relay apparatus 20 (S110, S140) periodically, to thereby confirm whether the communication connection with the relay apparatus 20 is active. As described later, when detecting the disconnection of the communication with the relay apparatus 20, the controller 10 generates an alarm (S120, S150), to notify the user of an abnormality.

An interval T20 of the transmission of the heartbeat signal (S130) after the transmission of the first signal may be shorter than an interval T10 of the transmission of the heartbeat signal (S100) before the transmission of the first signal. For example, the interval of the transmission of the heartbeat signal is normally set to the interval of two seconds, and set to the interval of 0.2 seconds after the transmission of the first signal (continuous increase signal).

In the above, description has been made by taking the case where the set value is increased as an example. However, needless to say, the same is true of the case where the set value is decreased.

Figure 6:
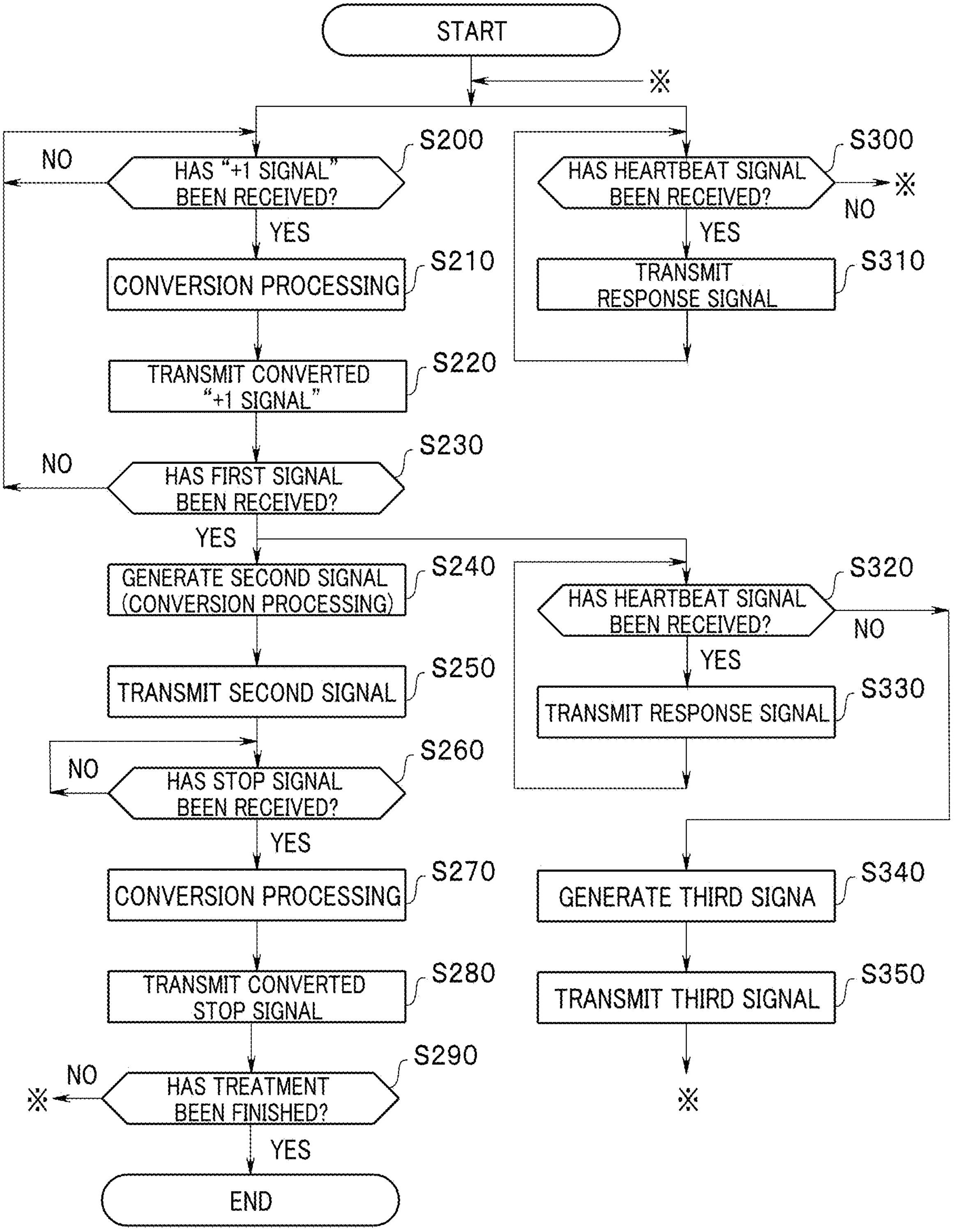
FIG. 6 is a flowchart at a time of communication disconnection of the medical system of the embodiment.

Next, the operation of the relay apparatus 20 will be described with reference to the flowchart in FIG. 6.

<Step S200-S220>

When the reception unit 21A of the relay apparatus 20 receives the "+1 signal" from the controller 10, the conversion unit 23 converts the "+1 signal" into a "converted +1 signal" corresponding to a communication specification of the electric scalpel device 30D, and the transmission unit 21B transmits the "converted+1 signal" to the electric scalpel device 30D. As a result, the output value of the electric scalpel device 30D increases to "51" as shown in FIG. 5.

<Step S230-S250>

When the reception unit 21A of the relay apparatus 20 receives, from the controller 10, the first signal that continuously increases the set value of the electric scalpel device 30D, the conversion unit 23 converts the "+1 signal" into the second signal corresponding to the communication specification of the electric scalpel device 30D, and the transmission unit 21B transmits the second signal to the electric scalpel device 30D.

<Step S260-S280>

When the reception unit 21A of the relay apparatus 20 receives, from the controller 10, the stop signal that stops the continuous increase of the set value of the electric scalpel device 30D, the conversion unit 23 converts the stop signal into a converted stop signal corresponding to the communication specification of the electric scalpel device 30D, and the transmission unit 21B transmits the converted stop signal to the electric scalpel device 30D.

<Step S290>

Until the treatment is finished (S290: YES), the processing will be repeated from the step S200.

The communication unit 21 of the relay apparatus 20 repeats the reception of the heartbeat signal (S300, S320) and the transmission of the response signal (S310, S330) periodically, to confirm whether the communication connection with the controller 10 is active. As already described above, the interval T20 of the reception of the heartbeat signal (S320) after the reception of the first signal may be shorter than the interval T10 of the reception of the heartbeat signal (S300) before the reception of the first signal.

Note that if no heartbeat signal can be received in the step S300 (NO), the relay apparatus 20 may generate an alarm to notify the user.

<Step S320-S350>

If no heartbeat signal can be received (S320, NO), the relay apparatus 20 generates the third signal as the fail-safe signal for stopping the increase of the set value of the electric scalpel device 30D, and transmits the third signal to the electric scalpel device 30D. With the fail-safe signal, the set value of the electric scalpel device 30D does not increase beyond the user's intended value. The fail-safe signal is a command signal that controls the electric scalpel device 30D to operate on the safe side assumed at the time of design.

In the present embodiment, the third signal (fail-safe signal) is the signal that stops changing the set value, the signal having been converted in accordance with the protocol of the medical device 30, that is, the converted stop signal. When the electric scalpel device 30D receives the third signal, the increase of the set value of the electric scalpel device 30D stops.

Figure 7:
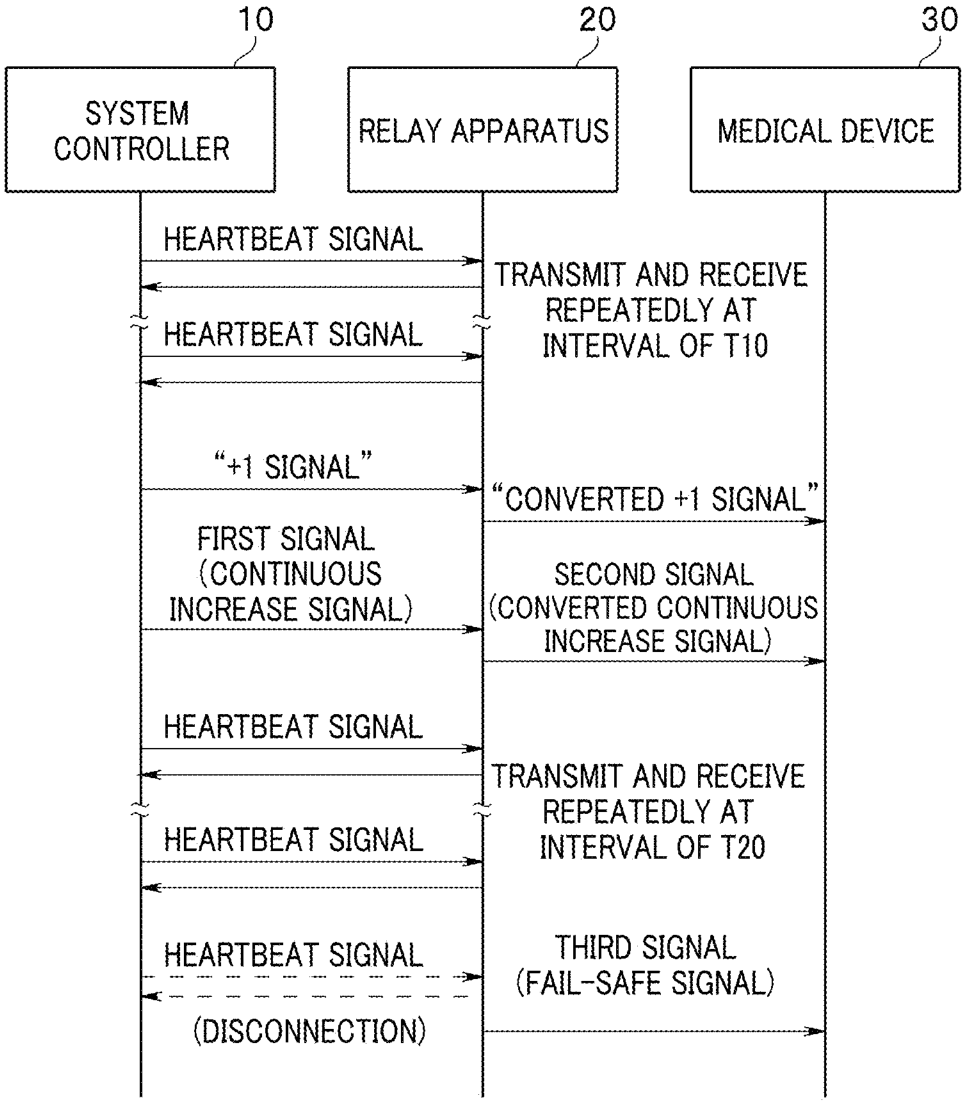
FIG. 7 is a sequence diagram of the medical system of the embodiment.

FIG. 7 is a view of a communication sequence of the medical system 1.

The controller 10 and the relay apparatus 20 transmit and receive the heartbeat signal therebetween at the predetermined interval T10, to confirm whether the communication connection is active.

When receiving the "+1 signal" from the controller 10, the relay apparatus 20 transmits the "converted +1 signal" to the medical device 30.

When receiving the first signal (continuous increase signal) from the controller 10, the relay apparatus 20 transmits the second signal (converted increase signal) to the medical device 30.

The controller 10 and the relay apparatus 20 transmit and receive the heartbeat signal therebetween at the predetermined interval T20, to confirm whether the communication connection is active.

When the relay apparatus 20 cannot receive the heartbeat signal, the relay apparatus 20 transmits the third signal to the medical device 30. With the third signal, the increase of the set value of the medical device 30, which has been increasing continuously, stops.

As described above, the present embodiment is capable of providing the relay apparatus of the medical system, which is configured to control the medical device 30 to perform the fail-safe operation, even if the communication between the controller 10 and the relay apparatus 20 is disconnected in the medical system 1 including the controller 10, the relay apparatus 20, and the medical device 30. The present embodiment is also capable of providing the control method for the relay apparatus 20 of the medical system, which controls the medical device 30 to perform the fail-safe operation, even if the communication between the controller 10 and the relay apparatus 20 is disconnected. The present embodiment is further capable of providing the medical system including the medical device 30 that performs the fail-safe operation even if the communication between the controller 10 and the relay apparatus 20 is disconnected.

Modification of Embodiment

A medical system of a modification of the embodiment is similar to and has the same effects as those of the medical system of the embodiment. Therefore, the same constituent elements having the same functions as those in the medical system of the embodiment are attached with the same reference signs and descriptions thereof will be omitted.

When receiving the first signal, the relay apparatus 20 of the medical system 1 generates the second signal (continuous UP signal) that changes the set value at the predetermined rate and outputs the generated second signal. In contrast, when a relay apparatus 20 of the present modification receives the first signal, the relay apparatus 20 may generate a second signal in which the "+1 signal" that changes the set value in a set minimum unit is continuous at a predetermined frequency.

The third signal is not limited to the stop signal that stops the change in the set value, as long as it is a fail-safe signal that causes the medical device 30 to be in a safe state. For example, the third signal may be a control signal that sets the set value to be a first set value previously set for each of the medical devices.

Table 1 shows an example of a table of the first set values stored in the memory.

TABLE 1

| medical device | function | set range | first set value |
|---|---|---|---|
| video processor | brightness | −8~+8 | 0 |
| electric scalpel device | output | 1~100 | 1 |
| pneumoperitoneum device | pressures | 3~25 | 3 |

The first set values for the output of the electric scalpel device 30D and the pressure of the pneumoperitoneum device 30G are the lowest values of the set values. In contrast, the first set value of a brightness value of the video processor 30A is a medium value of the set value.

The third signal as the fail-safe signal may include an alarm signal, in addition to the control signal that controls the set value of the medical device 30 so that the medical device 30 is in the safe state. Upon receipt of the alarm signal, for example, the medical device 30 may notify a communication disconnection with voice or turn on a lamp for notifying an abnormality, for example.

Note that, as described above with reference to FIG. 3, also the detection unit 12 of the controller 10 detects the communication disconnection between the controller 10 and the relay apparatus 20, based on the heartbeat signal or the strength of the wireless signal. If the controller 10 detects the communication disconnection between itself and the relay apparatus 20 connected to a certain medical device 30, the controller 10 generates an alarm (FIG. 3; S120, S150). The alarm may be notified by turning the screen for the certain medical device 30 on the touch panel to be black (blackout) or with voice, for example.

The present disclosure is not limited to the above-described embodiments, and the like, but various changes, modifications, etc., are possible without changing the gist of the present disclosure.

What is claimed is:

1. A relay apparatus of a medical system, comprising:

a reception unit configured to receive a heartbeat signal from a controller of the medical system, the reception unit being configured to, after receiving a first signal that continuously changes a set value of a medical device of the medical system, receive the heartbeat signal at a shorter interval than an interval before receiving the first signal;

a conversion unit configured to convert the first signal into a second signal;

a transmission unit configured to transmit the second signal to the medical device;

a detection unit configured to detect a communication disconnection between the relay apparatus and the controller, based on the heartbeat signal received at the shorter interval; and a control unit configured to control the transmission unit to transmit a third signal, which is a fail-safe signal, to the medical device, based on a detection signal received from the detection unit.

2. The relay apparatus of the medical system according to claim 1, wherein the first signal is a signal that changes the set value at a predetermined rate.

3. The relay apparatus of the medical system according to claim 2, wherein the second signal is a signal that changes the set value at a predetermined rate.

4. The relay apparatus of the medical system according to claim 2, wherein the second signal is a signal in which a signal that changes the set value is continuous.

5. The relay apparatus of the medical system according to claim 1, wherein the third signal is a signal that stops a change in the set value.

6. The relay apparatus of the medical system according to claim 1, wherein the third signal is a signal that changes the set value to a predetermined first set value.

7. The relay apparatus of the medical system according to claim 6, further comprising a memory that stores the first set value corresponding to the medical device.

8. The relay apparatus of the medical system according to claim 6, wherein the first set value is a lowest value of the set value.

9. The relay apparatus of the medical system according to claim 1, wherein the third signal includes an alarm signal.

10. A control method for a relay apparatus of a medical system, comprising:

receiving a heartbeat signal from a controller of the medical system, and upon reception of a first signal that continuously changes a set value of a medical device of the medical system, receiving the heartbeat signal at a shorter interval than an interval before receiving of the first signal;

converting the first signal into a second signal;

transmitting the second signal to the medical device; and upon detection of a communication disconnection based on the heartbeat signal received from the controller at the shorter interval, transmitting a third signal, which is a fail-safe signal, to the medical device.

11. A medical system comprising:

a medical device;

a controller configured to transmit a heartbeat signal to a relay apparatus of the medical system, the controller being configured to, after transmitting a first signal that continuously changes a set value of the medical device to the relay apparatus, transmit the heartbeat signal at a shorter interval than an interval before transmitting the first signal; and the relay apparatus configured to: receive the first signal to convert the received first signal into a second signal; transmit the second signal to the medical device; and upon detection of a communication disconnection between the relay apparatus and the controller based on the heartbeat signal received at the shorter interval, transmit a third signal, which is a fail-safe signal, to the medical device.

12. The medical system according to claim 11, wherein, the controller generates an alarm, upon detection of the communication disconnection between the controller and the relay apparatus.

* * * * *